US006413785B1

(12) United States Patent
Wilson et al.

(10) Patent No.: US 6,413,785 B1
(45) Date of Patent: Jul. 2, 2002

(54) SOLID PHASE SYNTHESIS OF 1-AMINOHYDANTOINS

(75) Inventors: Lawrence Joseph Wilson, Mason; David Edward Portlock, Maineville; Min Li, West Chester, all of OH (US)

(73) Assignee: The Procter & Gamble Co., Cincinnati, OH (US)

( * ) Notice: Subject to any disclaimer, the term of this patent is extended or adjusted under 35 U.S.C. 154(b) by 0 days.

(21) Appl. No.: 09/622,609
(22) PCT Filed: Feb. 15, 1999
(86) PCT No.: PCT/IB99/00266
§ 371 (c)(1),
(2), (4) Date: Aug. 18, 2000
(87) PCT Pub. No.: WO99/42450
PCT Pub. Date: Aug. 26, 1999

Related U.S. Application Data
(60) Provisional application No. 60/075,395, filed on Feb. 20, 1998.

(51) Int. Cl.$^7$ .................. G01N 33/543; C07D 233/40; A61K 38/00
(52) U.S. Cl. .................. 436/518; 548/317.1; 530/334; 530/335
(58) Field of Search ...................... 436/518; 548/317.1; 530/334, 335

(56) References Cited

U.S. PATENT DOCUMENTS

| 4,363,916 A | 12/1982 | Fukui et al. ................. 548/313 |
| 5,324,483 A | 6/1994 | Cody et al. .................. 422/131 |
| 5,462,940 A | 10/1995 | Yu et al. .................... 514/235.8 |

FOREIGN PATENT DOCUMENTS

| EP | 0126849 A1 | 12/1984 | ......... C07D/233/80 |
| EP | 0284202 A1 | 9/1988 | ......... C07D/233/80 |

OTHER PUBLICATIONS

Wilson et al., "Solid Phase Synthesis of 1–Aminohydantoin Libraries", *Tetrahedron Letters*, vol. 39, pp. 5135–5138 (1998).
Hanessian et al., "Solution and Solid Phase Synthesis of 5–Alkoxyhydantoin Libraries With a Three–Fold Functional Diversity", *Tetrahedron Letters*, vol. 37, pp. 5835–5838 (1996).
Gut et al., "Reaction of Six–Membered Cyclic Hydrazides With Aromatic Aldehydes", *Collection Czechoslov. Chem. Commun.*, vol. 33, pp. 2087–2096 (1968).
Barraclough et al., "Synthesis of Hexahydrocyclopentimidazol-2-(1H)-one Derivatives Displaying Selective DP–Receptor Agonist Properties", *Bioorganic & Medicinal Chem.*, vol. 4, No. 1, pp. 81–90 (1996).
Hutchins et al., "A General Method for the Solid Phase Synthesis of Ureas", *Tetrahedron Letters*, vol. 35, No. 24, pp. 4055–4058 (1994).

Hamaker et al., "Automated Solid Phase Organic Synthesis VII. Triphosgene Employed in the Synthesis of N,N'-Unsymmetrically Disubstituted Ureas", presented at CHI's *Solid Phase Synthesis: Developing Small Molecule Libraries*, Coronado, CA., Feb. 1–2, 1996.

Vidal et al., "Electrophilic Amination: Preparation and Use of N–Boc–3–(4–cyanophenyl)oxaziridine, a New Reagent That Transfers a N–Boc Group to N– and C–Nucleophiles", *J. Org. Chem.*, vol. 58, pp. 4791–4793 (1993).

Klinguer et al., "Synthesis of Hydrazinopeptides Using Solid Phase N–Amination. Application to Chemical Ligation", *Tetrahedron Letters*, vol. 37, pp. 7259–7262 (1996).

Carpino, L.A., "O–Acylhydroxylamines. II. O–Mesitylenesulfonyl–, O–p–Toluenesulfonyl– and O–Mesitoylhydroxylamine", *O–Acylhydroxylamines*, vol. 82, pp. 3133–3135 (1960).

Gever et al., "ALkylhydrazines", (Contribution from the Division of Chemistry, Eaton Laboratories, Inc.), pp. 813–819 (1949).

Davies et al., "Selectivity in the Trimethylsilylation and Acylation of Peptide Bonds, and its Application to Modification of the Enkephalins", *J. Chem. Soc. Perkin Trans. I*, pp. 2939–2947 (1982).

Xiao et al., "Selective Solid Phase Synthesis of Ureas and Hydantoins from Common Phenyl Carbamate Intermediates", *J. Org. Chem.*, vol. 62, pp. 6968–6973 (1997).

Matthews et al., "Base–Promoted Solid–Phase Synthesis of Substituted Hydantoins and Thiohydantoins", *J. Org. Chem.*, vol. 62, pp. 6090–6092 (1997).

(List continued on next page.)

*Primary Examiner*—Padmashri Ponnaluri
*Assistant Examiner*—Steven C. Tizio
(74) *Attorney, Agent, or Firm*—Richard S. Echler, Sr.; Carl J. Roof; Milton B. Graff

(57) ABSTRACT

The subject invention involves processes for making 1-aminohydantoin compounds using a solid support resin, comprising the following steps; (a) preparing a resin-bound protected α-hydrazinyl ester; (1) by reacting the resin with an α-bromo carboxylic acid, then with a protected hydrazine; or (2) by reacting the resin with a protected α-hydrazinyl carboxylic acid; (b) preparing a resin-bound imine by removing the blocking group from the hydrazinyl moiety, then reacting the unprotected hydrazinyl moiety with an aldehyde or ketone; (c) preparing a resin-bound secondary urea: (1) by reacting the imine with p-nitrophenylchloroformate or trisphosgene, then with a primary amine; or (2) by reacting the imine with an isocyanate, and (d) preparing the 1-aminohydantoin compound by removing the secondary urea from the resin and cyclizing it.

16 Claims, No Drawings

OTHER PUBLICATIONS

Dressman et al., "Solid Phase Synthesis of Hydantoins Using a Carbamate Linker and a Novel Cyclization/Cleavage Step", *Tetrahedron Letters,* vol. 37, No. 7, pp. 937–940 (1996).

Short et al., "The Synthesis of Hydantoin 4–Imides on Solid Support", *Tetrahedron Letters,* vol. 37, No. 42, pp. 7489–7492 (1996).

Kim et al., "Solid Phase Synthesis of Hydantoin Library Using a Novel Cyclization and Traceless Cleavage Step", *Tetrahedron Letters,* vol. 38, No. 26, pp. 4603–4606 (1997).

Hoffman et al., "The Preparation of 2–Hydrazinyl Esters in High Optical Purity From 2–Sulfonyloxy Esters", *Tetrahedron Letters*, vol. 31, No. 21, pp. 2953–2956 (1990).

DeWitt et al., "Diversomers: An Approach to Nonpeptide, Nonoligmeric Chemical Diversity", *Proc. Natl. Acad. Sci.,* vol. 90, pp. 6909–6913 (1993).

Scott et al., "Solid Phase Organic Synthesis (SPOS): A Novel Route to Diketopiperazines and Diketomorpholines", *ESCOM Molecular Diversity*, pp. 125–134 (1995).

SOLID PHASE SYNTHESIS OF 1-AMINOHYDANTOINS

This application claims the benefit of provisional application No. 60/075,395 file Feb. 20, 1998.

TECHNICAL FIELD

The subject invention relates to methods for synthesizing 1-aminohydantoin compounds, using a solid-support resin to facilitate purification of intermediates.

BACKGROUND OF THE INVENTION

Resin based chemistry methods have blossomed the past decade, and have proved to be highly useful for multi-step syntheses.

Interest in compounds having the 1-amino variant of the hydantoin nucleus (1-below) stems from the demonstrated commercial significance as anti-infective (e.g., nitrofurantoin (2)), skeletal smooth muscle relaxant (e.g., dantrium (3)), anti-arrhythmic (e.g., azimilide (4)), and other interesting pharmacological diversity (e.g., prostaglandin D receptor agonist (5)) of different species.

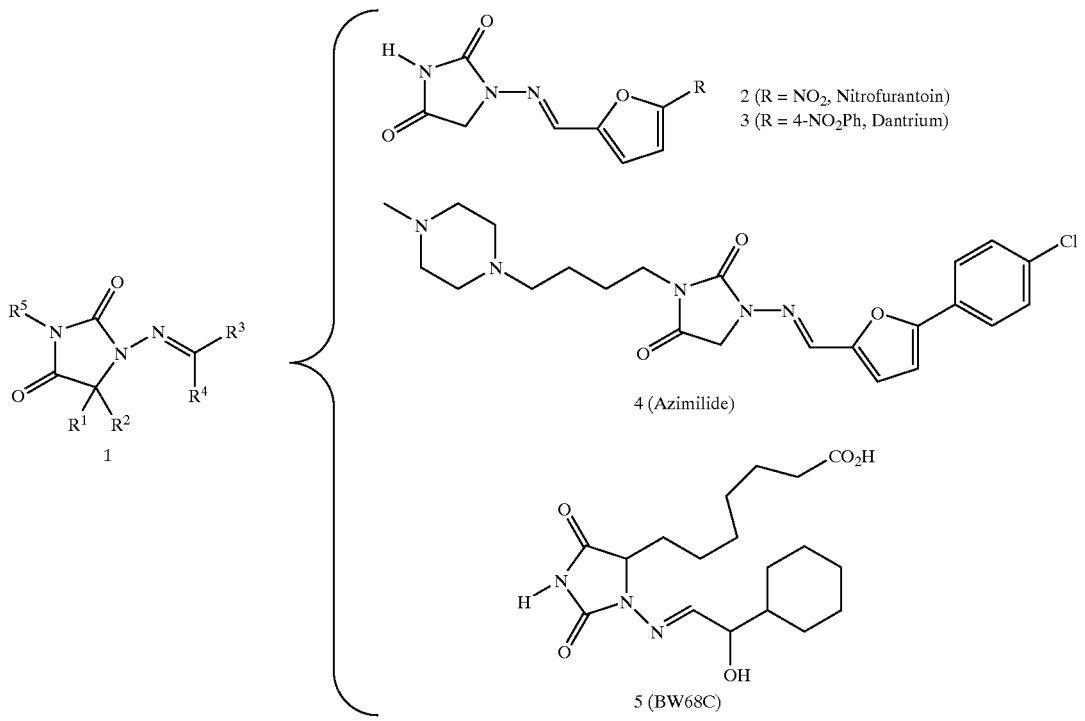

Furthermore, the 1-aminohydantoins contain the aza surrogate of amino acids (i.e. hydrazino acids), and aza amino acid replacements have pharmacological significance in many therapeutic areas. This aza replacement adds significantly different chemical and physical properties to the hydantoin ring system; one example of this is stable imine formation at the 1-amino position (semicarbazone-like).

Currently known solid phase based hydantoin routes that utilize cyclizative cleavage are disclosed in: (a) Dewitt, S. H.; Kiely, J. S.; Stankovic, C. J.; Schroeder, M. C.; Reynolds Cody, D. M.; Pavia, M. R.; *Proc. Natl. Acad. Sci.,*, vol. 90 (1993), pp. 6909–6913; (b) Dressman, B. A.; Spangle, L. A.; Kaldor, S. W.; *Tetrahedron Lett.*, vol. 37 (1996), pp. 937–940; (c) Hanessian, S.; Yang, R.-Y.; *Tetrahedron Lett.*, vol. 37 (1996), pp. 5835–5838; (d) Kim, S. W.; Ahn, S. Y.; Koh, J. S.; Lee, J. H.; Ro, S.; Cho, H. Y.; *Tetrahedron Lett,* vol. 38 (1997), pp. 4603–4606; (e) Matthews, J.; Rivero, R. A.; *J. Org. Chem.*, vol. 62 (1997), pp. 6090–6092. For an example of amine displacements on α-bromo resin esters, see: Scott, B. O.; Siegmund, A. C.; Marlowe, C. K.; Pei, Y.; Spear, K. L.; *Molecular Diversity,* vol. 1 (1995), pp. 125–134.

Solution based chemist methods for making 1-aminohydantoins are disclosed, for example, in European Patent Application No. 0 126 849 of the Wellcome Foundation, inventor Caldwell, published Dec. 5, 1984.

SUMMARY OF THE INVENTION

The subject invention involves processes for making 1-aminohydantoin compounds:

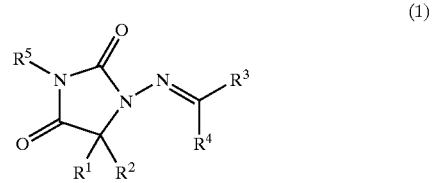

(1)

using a solid-support resin having a linking moiety capable of reacting with carboxylic acids and attaching them to the resin, comprising the following steps:

(a) preparing resin-bound, protected α-hydrazinyl esters;
 (1) by reacting the resin with α-bromo carboxylic acids; then with a protected hydrazine; or
 (2) by reacting the resin with protected α-hydrazinyl carboxylic acids;
(b) preparing resin-bound imines by removing the blocking group from the hydrazinyl moiety of the α-hydrazinyl esters, then reacting the unprotected hydrazinyl moiety with aldehydes or ketones;
(c) preparing resin-bound secondary ureas;
 (1) by reacting the resin-bound imines with p-nitrophenylchloroformate or triphosgene, then with primary amines; or
 (2) by reacting the resin-bound imines with isocyanates; and
(d) preparing the 1-aminohydantoin compounds by removing the resin-bound secondary ureas from the resin and cyclizing them.

DETAILED DESCRIPTION OF THE INVENTION

As used herein unless specified otherwise, "takyl" means a hydrocarbon chain which is branched linear or cyclic, saturated or unsaturated (but not aromatic), substituted or unsubstituted. The term "alkyl" may be used alone or as part of another word where it may be shortened to "alk" (e.g., in alkoxy, alkylamino). Preferred alkyl have from one to about 28 carbon atoms, preferably from one to about twelve carbon atoms, more preferably from one to about six carbon atoms, more preferably still from one to about four carbon atoms; most preferred are methyl or ethyl. Preferred cyclic and branched allyl have from three to about 28 carbon atoms, preferably from three to about twelve carbon atoms, more preferably from three to about six carbon atoms. Preferred cyclic alkyl have one hydrocarbon ring, but they may have two or three or more fused hydrocarbon rings. Preferred alkyl are unsaturated with from one to about three double and/or triple bonds; preferably they are mono-unsaturated with one double bond; more preferred alkyl are saturated. Preferred substituents of alkyl include aryl, heteroaryl, heterocycle, halo, nitro, cyano, hydroxy, thio, amino, carboxy, acyl, amide (the last six being unsubstituted or substituted with one, or two or three if possible, alkyl, aryl, heterocycle or heteroaryl). More preferred substituents of alkyl include aryl, heteroaryl, heterocycle, fluoro, alkoxy, aryloxy, alkylthio, arylthio, dialkylamino, arylalkylamino, diarylamino, carboxy alkyl and aryl esters, alkylacyl, arylacyl, secondary and tertiary amides. More preferred alkyl are unsubstituted.

As used herein unless specified otherwise, "aryl" means an aromatic hydrocarbon ring which is substituted or unsubstituted. The term "aryl" may be used alone or as part of another word (e.g., in aryloxy, arylacyl). Preferred aryl have from six to about ten carbon atoms in the aromatic ring(s), and a total of from about six to about 28, preferably to about twelve, carbon atoms. Preferred aryl is phenyl or naphthyl; most preferred is phenyl. Preferred substituents of aryl include alkyl, aryl, heteroaryl, heterocycle, halo, nitro, cyano, hydroxy, thio, amino, carboxy, acyl, amide (the last six being unsubstituted or substituted with one, or two or three if possible, alkyl, aryl, heterocycle or heteroaryl). More preferred substituents of aryl include alkyl, aryl, heteroaryl, heterocycle, halo, nitro, alkoxy, aryloxy, alkylthio, arylthio, dialkylamino, arylalkylamino, diarylamino, carboxy alkyl or aryl esters, alkylacyl, arylacyl, secondary and tertiary amides. More preferred aryl are unsubstituted.

As used herein, "heteroatom" means a nitrogen, oxygen, or sulfur atom.

As used herein unless specified otherwise, "heterocycle" means a cyclic alkyl with one or more heteroatoms in the hydrocarbon ring(s). Preferred heterocycles have from one to about six heteroatoms in the ring(s), more preferably one or two or three heteroatoms, most preferably one heteroatom. Preferred heterocycles have from three to about twelve carbon plus heteroatoms in the ring(s), more preferably from three to about seven; and a total of from three to about 28 carbon plus heteroatoms, more preferably from three to about twelve. Heterocycles are unsubstituted or substituted. Preferred heterocycle substituents are the same as for alkyl.

As used herein unless specified otherwise, "heteroaryl" means aromatic hydrocarbon ring(s) with one or more heteroatoms in the ring(s). Preferred heteroaryls have from one to about six heteroatoms in the ring(s), more preferably one or two or three heteroatoms, most preferably one heteroatom. Preferred heteroaryls have from five to about twelve carbon plus heteroatoms in the aromatic ring(s), more preferably from five to about nine; and a total of from five to about 28 carbon plus heteroatoms, more preferably from five to about twelve. Heteroaryls are unsubstituted or substituted. Preferred heteroaryl substituents are the same as for aryl.

As used herein, "B1" is a protecting group, many of which are well known. Preferred protecting groups include t-butyloxycarbonyl (BOC), 9-fluorenylmethoxycarbonyl (FMOC), allyloxycarbonyl (ALLOC), trimethylsilylethoxy-carbonyl (TEOC); particularly preferred is BOC.

The subject invention processes involve the use of solid-support resins which are well known. The solid support resins used for the subject processes have a linking moiety capable of reacting with carboxylic acids and attaching them to the resin. Preferred resins have a free hydroxy moiety as part of the linking moiety of the resin; more preferred resins have a hydroxymethyl linking moiety. A particularly preferred resin is bydroxymethylpolystyrene.

The first step of a subject invention process involves preparing a resin-bound, protected α-hydrazinyl ester:

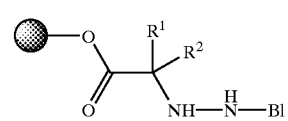

(9)

The resin-bound, protected α-hydrazinyl ester can be made by reacting the resin with an α-bromo carboxylic acid:

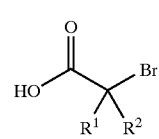

(7)

$R^1$ and $R^2$ are each independently any moiety that is stable throughout the subject process and in the final product. Preferred $R^1$ and $R^2$ include hydrogen, alky, aryl, heterocycle, heteroaryl. It is preferred that either one or both of $R^1$ and $R^2$ be hydrogen. More preferred non-hydrogen $R^1$ and $R^2$ include alkyl and aryl.

The material resulting from the reaction of the resin with the α-bromo carboxylic acid is then reacted with a protected hydrazine:

B1—NHNH$_2$.

An alternative method for preparing 9 involves reacting the resin with a protected α-hydrazinyl carboxylic acid:

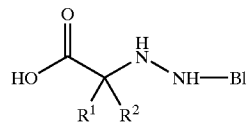
(8)

The second step of a subject invention process involves preparing a resin-bound imine:

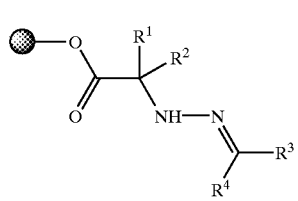
(12)

The resin-bound imine is prepared by removing the blocking group from the hydrazinyl moiety of 9 by any known method.

The resulting material is reacted with an aldehyde: R$^3$CHO, or ketone: R$^3$R$^4$CO, under conditions such that the unprotected hydrazinyl moiety reacts with the aldehyde or ketone producing imine 12.

R$^3$ and R$^4$ can be any moieties which provide stable intermediates and final product for the subject processes. R$^3$ and R$^4$ can be independent moieties or can be connected in a ring structure. Preferred R$^3$ and R$^4$ are each independently selected from hydrogen, alkyl, aryl, heterocycle, heteroaryl; or are bonded together forming a moiety selected from cycloalkyl, aryl, heterocycle, heteroaryl.

The third step of a subject invention process involves preparing a resin-bound secondary urea:

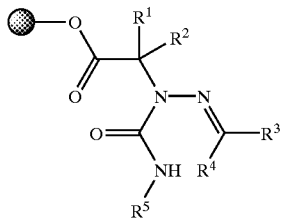
(15)

The resin-bound secondary urea can be made by reacting 12 with p-nitrophenylchloroformate (p-NO$_2$PhOC(O)Cl) or triphosgene. The resulting material is then reacted with a primary amine: R$^5$NH$_2$.

Alternatively, 15 can be made by reacting 12 with an isocyanate: R$^5$NCO.

R$^5$ can be any moiety which provides stable intermediates and a stable product for the subject processes. Preferred R$^5$ include hydrogen, alkyl, aryl, heterocycle, heteroaryl. More preferred R$^5$ include hydrogen, alkyl and aryl.

The fourth step of a subject invention process involves preparing a 1-aminohydantoin compound 1 by removing 15 from the resin and cyclizing it. In a preferred embodiment of the subject processes, the ring system is constructed utilizing a traceless cyclization-cleavage. This is preferably achieved by treating 15 with an amine base (e.g., triethylamine, diisopropylamine) or a silylating agent (e.g., trimethylsilyl trifluoromethanesulfonate, bistrimethylsilyl trifluoromethane-acetamide).

The subject invention processes are useful for making compounds individually or in libraries of separate or mixtures of compounds. The synthesis of libraries of compounds of structure 1 can readily be carried out using a multiple cell procedure, e.g., 96 plate format (e.g., Robbins Block, Advanced ChemTech 496), where different compounds having different combinations of R$^1$, R$^2$, R$^3$, R$^4$ and R$^5$ can be made in each cell simultaneously. Also, libraries of mixtures of compounds of structure 1 can be made by reacting reagents which are mixtures rather than single compounds. Both types of libraries are useful for rapid screening of numerous compounds for pharmacological and other activities.

Scheme I below is exemplary of the subject invention processes.

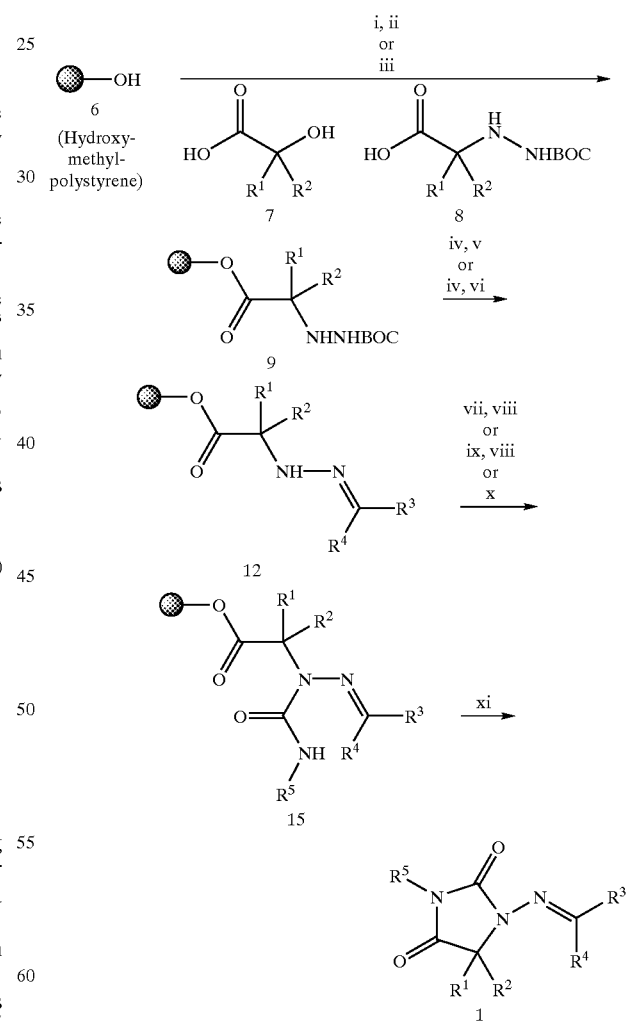

Reagents: (each reaction sequence is repeated once)—(i) 7, diisopropylcarbodiimide (DIC), dimethylaminopyridine (DMAP), 1,2-dichloroethaene (1,2-DCE), room temperature (rt); (ii) BOCNHNH$_2$, dimethylformamide (DMF), tetrabutylammonium iodide (TBAI), rt or heat (Δ); (iii) 8, PPh$_3$, diethylazidodicarboxylate (DEAD), dichloromethane (DCM)/tetrahydrofuran (THF) (1:1); (iv) trifluoroacetic acid (TFA), 1,2-DCE; (v) R$^3$CHO (10), DMF, diisopropylethylamine (DIPEA); (vi) R$^3$R$^4$CO (11), EtOH, acetic acid (AcOH), reflux; (vii) p-NO$_2$PhOC(O)Cl, DIPEA, THF-1,2-DCE (1:1); (viii) R$^5$NH$_2$ (13), DMF, DIPEA; (ix) triphosgene, DIPEA, 1,2-DCE; (x) R$^5$NCO (14), DMAP, DMF, (xi) bistrimethylsilyl trifluoromethaneacetamide (BSTFA), 1,2-DCE, reflux 8–24 hrs.

Regarding synthesis of hydrazinyl esters on the resin, coupling of hydroxymethylpolystyrene 6 with bromoacetic acid 7, followed by reaction with t-butylcarbazate results in an excellent yield when R$^1$ and R$^2$ are H. When trying to incorporate other moieties at the R$^1$ position through this method, a decrease in the loading of the desired ester 9 is observed in some cases. However, others, such as bromophenyl acetic acid, attach to the resin with high yield using this method. A distinct S$_N$2 type steric effect is believed to be the reason for lower yields in some instances. Direct coupling of the requisite hydrazinyl carboxylic acid building block 8 often provides better yield in such cases. These can be synthesized from the corresponding hydroxy acids via triflate displacement. (See Hoffman, R. V.; Kim, H.-O; *Tetrahedron Lett.,* vol. 31 (1990), pp. 2953–2956.) This also gives the option of introducing chirality at the alpha carbon. Preferred coupling conditions utilize a Mitsunobu esterification protocol. (See Spatola, A. F.; Darlak, K.; Romanvskis, P.; *Tetrahedron Lett.,* vol. 37 (1996), pp. 591–594.)

Deprotection of the BOC group under standard conditions is followed by condensation with an appropriate aldehyde 10 or ketone 11 to produce imine 12. This condensation proceeds smoothly at room temperature for many aldehydes, as evidenced by ninhydrin testing. The condensation proceeds with many ketones by heating the ketone and resin in either ethanol or 1,4-dioxane.

After imine 12 formation, three methods can be used to prepare the secondary urea 15, all of which can be successful but differ in yield of the final product. These three methods are: (a) treatment with p-NO$_2$PhOC(O)Cl, followed by amine displacement (procedures vii & viii) (see Hutchins, S. M.; Chapman, K. T.; *Tetrahedron Lett.,* vol. 35 (1994), pp. 4055–4058); (b) treatment with triphosgene, followed by amine displacement (procedures ix & viii); and (c) treatment with an isocyanate (procedure x).

The final step, the "traceless" cyclizative cleavage, requires mild conditions due to the potential instability of the imine bond of 15 towards hydrolysis (e.g. HCl and heating) and the likelihood of ring opening of the final product 1 under mild nucleophilic conditions (e.g., MeOH, NEt$_3$). Another potential side reaction is retro-isocyanate addition (15 to 12), which may occur under strongly basic conditions (KOH, MeOH). Silylation appears to provide the best results. Preferred conditions include treatment with BSTFA in 1,2-DCE at or near reflux (procedure xi). (See Davies, J. S.; Merritt, R. K; Treadgold, R. C.; *J. Chem. Soc. Perkin Trans. I,* 1982, pp. 2939–2947.) Under these conditions, the cyclization generally proceeds smoothly, releasing primarily hydantoin products into solution. The table below lists some selected examples and synthesis sequences.

| Example | Structure (1) | Procedures | Yield (%) |
| --- | --- | --- | --- |
| A | 4 (Azimilide) | i, ii, iv, v, vii, viii | 55 |
| B | 3 (Dantrium) | i, ii, iv, v, vii, viii | 36 |

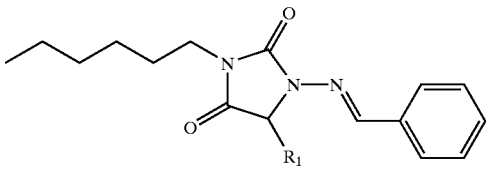

16 a–e

| | | | |
| --- | --- | --- | --- |
| C | 16a, R$^1$ = H | i, ii, iv, v, vii, viii | 45 |
| D | 16b, R$^1$ = Me | i, iii, iv, v, vii, viii | 44 |
| E | 16c, R$^1$ = i-Bu | i, iii, iv, v, vii, viii | 23 |
| F | 16d, R$^1$ = i-Pr | i, iii, iv, v, vii, viii | 20 |
| G | 16e, R$^1$ = n-Hex | i, ii, iv, v, vii, viii | 15 |
| H | | i, ii, iv, v, ix, viii | 58 |
| J | | i, ii, iv, v, x | 15 |

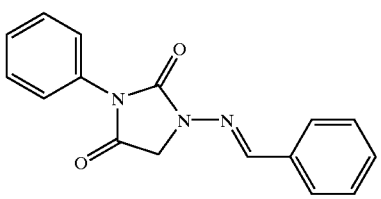

17

| Example | Structure (1) | Procedures | Yield (%) |
|---|---|---|---|
| K | 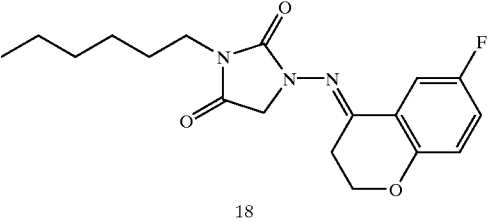 18 | i, ii, iv, vi, vii, viii | 20 |
| L | 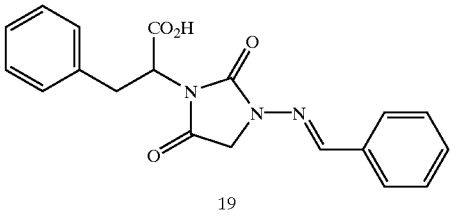 19 | i, ii, iv, v, vii, viii | 53 |
| M | 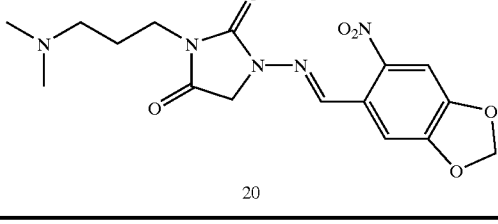 20 | i, ii, iv, v, vii, viii | 33 |

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of this invention.

What is claimed is:

1. A process for making 1-aminohydantoin compounds:

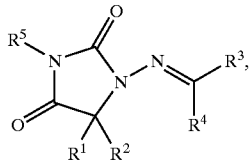

using a solid-support resin having a linking moiety capable of reacting with a carboxylic acid and attaching it to the resin, comprising the following steps:

(a) preparing a resin-bound, N-protected α-hydrazinyl ester:

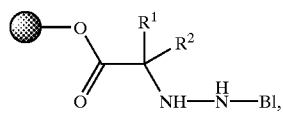

where B1 is a N-protecting group;
 (1) by reacting the resin with an α-bromo carboxylic acid, then with a N-protected hydrazine; or
 (2) by reacting the resin with a N-protected α-hydrazinyl carboxylic acid;

(b) preparing a resin-bound imine:

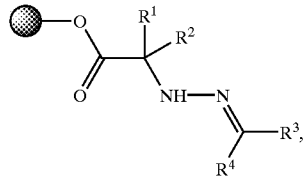

by removing the N-protecting group from the hydrazinyl moiety of the resin-bound, N-protected α-hydrazinyl ester; then reacting the unprotected hydrazinyl moiety with an aldehyde or a ketone;

(c) preparing a resin-bound secondary urea:

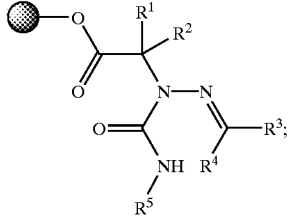

(1) by reacting the resin-bound imine with p-nitrophenylchloroformate or triphosgene, then with a primary amine; or
(2) by reacting the resin-bound imine with an isocyanate;

(d) preparing the 1-aminohydantoin compound by removing the resin-bound secondary urea from the resin and cyclizing it;

$R^1$, $R^2$, $R^3$, $R^4$ and $R^5$ each independently being any moiety that is stable throughout the process.

2. The process of claim 1 wherein:

(A) $R^1$, $R^2$ and $R^5$ are each independently selected from hydrogen, alkyl, aryl, heterocycle, and heteroaryl; $R^2$ preferably being hydrogen; and (B) $R^3$ and $R^4$ are each independently selected from hydrogen, alkyl, aryl, heterocycle, and heteroaryl; or $R^3$ and $R^4$ are attached forming a moiety selected from cycloalkyl, aryl, heterocycle, and heteroaryl.

3. The process of claim 2 wherein step (d) is a traceless cyclization cleavage achieved by treating the resin-bound secondary urea with an amine base or a silylating agent.

4. The process of claim 3 wherein the resin has a free hydroxy moiety.

5. The process of claim 3 wherein step (a)(1) is used, and step (a)(2) is not used.

6. The process of claim 3 wherein step (a)(2) is used, and step (a)(1) is not used.

7. The process of claim 3 wherein step (c)(2) is used and step (c)(1) is not used.

8. The process of claim 3 wherein step (c)(1) is used, and step (c)(2) is not used.

9. The process of claim 8 wherein in step (c)(1) p-nitrophenylchloroformate is used, and in step (d) a silylating agent is used.

10. The process of claim 8 wherein in step (c)(1) triphosgene is used, and in step (d) a silylating agent is used.

11. The process of claim 3 wherein in step (b) the hydrazinyl moiety is reacted with an aldehyde, and in step (d) a silylating agent is used.

12. The process of claim 3 wherein in step (b) the hydrazinyl moiety is reacted with a ketone, and in step (d) a silylating agent is used.

13. The process of claim 8 wherein $R^2$ is hydrogen, and in step (d) a silylating agent is used.

14. The process of claim 3 wherein $R^2$ is hydrogen.

15. The process of claim 14 wherein the resin is hydroxymethylpolystyrene.

16. The process of claim 15 wherein in step (d) the silylating agent bistrimethylsilyl trifluoromethaneacetamide is used.

* * * * *

UNITED STATES PATENT AND TRADEMARK OFFICE
CERTIFICATE OF CORRECTION

PATENT NO.     : 6,413,785 B1
DATED          : July 2, 2002
INVENTOR(S)    : Lawrence J. Wilson et al.

It is certified that error appears in the above-identified patent and that said Letters Patent is hereby corrected as shown below:

<u>Title page,</u>
Item [56], References Cited, OTHER PUBLICATIONS, "Gever et al.", please delete "Alkylhydrazines" and insert -- Alkylhydrazines --.

<u>Column 3,</u>
Line 22, please delete "takyl" and insert -- alkyl --.

Signed and Sealed this

Thirteenth Day of January, 2004

JON W. DUDAS
*Acting Director of the United States Patent and Trademark Office*